(12) United States Patent
Habtemariam et al.

(10) Patent No.: US 6,313,099 B1
(45) Date of Patent: *Nov. 6, 2001

(54) USE OF STEREOISOMERS OF CALENDULA GYLCOSIDES FOR THE TREATMENT OF PSORIASIS

(75) Inventors: Solomon Habtemariam, London; William Howard Stimson, Glasgow; Alexander Irvine Gray, Glasgow; Chaman Lal Anand, Glasgow; Peter George Waterman, Johnstone, all of (GB)

(73) Assignee: University of Strathclyde, Glasglow (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/355,056

(22) PCT Filed: Jan. 23, 1998

(86) PCT No.: PCT/GB98/00183

§ 371 Date: Jan. 24, 2000

§ 102(e) Date: Jan. 24, 2000

(87) PCT Pub. No.: WO98/32761

PCT Pub. Date: Jul. 30, 1998

(30) Foreign Application Priority Data

Jan. 24, 1997 (GB) .................................................. 9701415

(51) Int. Cl.[7] .................................................. A61K 31/70

(52) U.S. Cl. .............................. 514/25; 514/27; 514/860; 514/861; 514/863; 514/864; 536/4.1; 536/18.1

(58) Field of Search ............................ 514/25, 27, 860, 514/861, 863, 864; 536/4.1, 18.1

(56) References Cited

FOREIGN PATENT DOCUMENTS

| 38 36 519A1 | 5/1990 | (DE) . |
|---|---|---|
| 63041495 * | 2/1988 | (JP) . |
| WO89/05651A1 | 6/1989 | (WO) . |
| WO91/15218A1 | 10/1991 | (WO) . |
| WO97/04788A2 | 2/1997 | (WO) . |

OTHER PUBLICATIONS

Takaoka et al. "The Structures of Sesquiterpene Glycosides from *Pittosporum tobira* Ait", Chemistry Letters, vol. 7: 1121–1124, 1986.*

Takaoka et al., The structures of sesquiterpene glycosides from *Pittosporum tobira* Ait, Tennen Yuki Kagobutsu Toronkai Koen Yoshishu, vol. 28: 240–247, 1986.*

Etoh et al. "Stilbene glucoside esters and their related compounds as repellants against the ble mussel, *Mytilus edulis*", Nippon Kagaku Kaishi, vol. 5: 542–547, 1991.*

"Sequiterpene Glycosides Based On The Alloaromaden–Drane Skeleton From *CalendulaArvensis*"; Phytochemistry; vol. 27, No. 7, 1988; pp. 2205–2208.

"Sesquiterpene Glycosides From *CalendulaPersica*"; Planta Medica; vol. 54, No. 3, Jun. 1988; pp. 254–256.

"Structure And In Vitro Antiviral Activity OfSesquiterpene Glycosides From *CalendulaArvensis*"; Journal Of Natural Products; vol. 53, No. 4, Jul. 1990; pp. 830–835.

* cited by examiner

Primary Examiner—Ralph Gitomer
Assistant Examiner—D. Khare
(74) Attorney, Agent, or Firm—Alston & Bird LLP

(57) ABSTRACT

Use of stereoisomeric glycosidic compounds of formula (I) as pharmaceutical agents against psoriasis, compounds therefor and pharmaceutical formulations thereof wherein $R^1$ and $R^2$ are independently selected from —H, —OH, (1) and (2) and related esters and ethers thereto; $R^3$ is selected from —H, (3), (4), (5), (6), (7) and (8) and related esters and ethers thereto; $R^4$ is (9); $R^5$ is selected from the group —CH$_3$, —CHO, —COOH, —CH$_2$OH and related esters and ethers thereto; R$^6$ is selected from —OH, (10), (11), (12), (13) and (14) in the preparation of a medicament for the treatment of disease involving hyperproliferation of dermis cells.

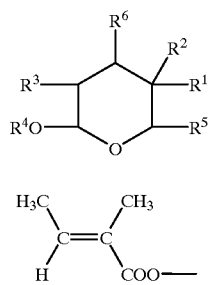

(I)

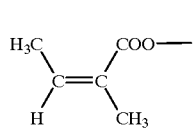

(1)

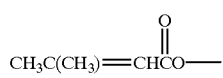

(2)

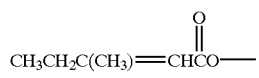

(3)

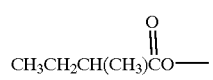

(4)

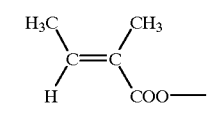

(5)

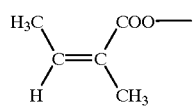

(6)

(7)

-continued

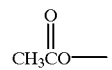
(8)

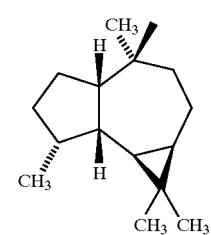

(9)

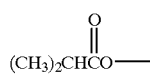

(10)

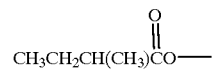

(11)

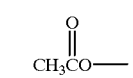

(12)

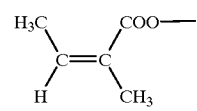

(13)

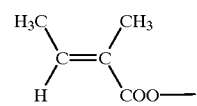

(14)

23 Claims, 2 Drawing Sheets

Figure 1:
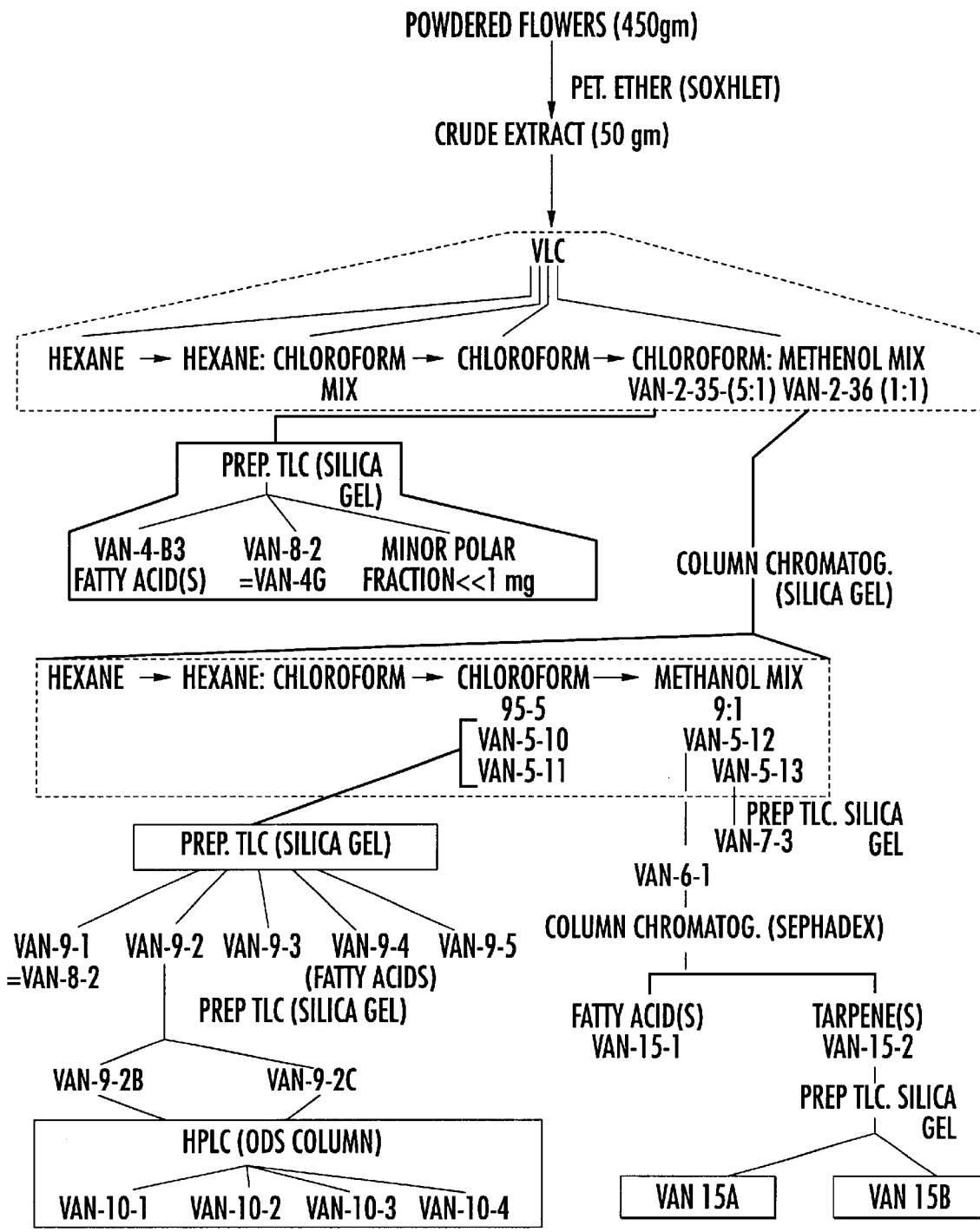

COMPARISON OF THE EFFECT OF SSSB CREAM, BETNOVATE AND PLACEBO IN A GROUP OF 7 PATIENTS WITH PSORIASIS. THE SYMPTOM SCORE IS DERIVED FROM GRADING 10 SYMPTOMS ON A SCALE OF 0 TO 3: ITCH, IRRITATION, RAWNESS OF SKIN FEELING OF HEAT, BLEEDING, SCALING, DISTURBED SLEEP, SCRATCHY FEELING, COSMETIC ANXIETY, AND PAIIN IN SKIN LESIONS.

USE OF STEREOISOMERS OF CALENDULA GYLCOSIDES FOR THE TREATMENT OF PSORIASIS

FIELD OF THE INVENTION

The present invention relates to certain glycoside containing compounds which are indicated as having an inhibiting effect on cell proliferation. More specifically the invention relates to sesquiterpene glycosides having a cytostatic effect on cells, and their use as cytostatic agents, in particular in the treatment of psoriasis.

BACKGROUND OF THE INVENTION

Crude Calendula plant extracts have been used in medicinal folklore for the treatment of several ailments for centuries. Such extracts have, for example, been used as or in anti-inflammatory medicaments and the like.

International patent application WO 91/15218 teaches a therapeutic composition against psoriasis comprising as active ingredient a solvent extract of at least six different herbs. This application teaches that marigold decoctions can be used against gastric and intestinal ulcers externally as well as for packing slowly healing wounds and ulcers. Nowhere is it stated that marigold extract is in fact used by itself as the active component in a therapeutical composition against psoriasis.

Pizza C., and de Tommasi N., Phytochemistry, Vol. 27, number 7, pp 2205–2208 (1988) teaches the isolation of and structure of a sesquiterpene glycoside from Calendula Arvensis. It is stated that Calendula Arvensis L. (Compositae) is an herbaceous plant used in Italian folk medicine as an anti-inflammatory and anti-pyretic remedy. There is no suggestion that the sesquiterpene glycosides obtained had cytostatic activity or could be used in the treatment of psoriasis.

Mascolo N. et al., Phytotherapy Research, Vo. 1, pp 28–31 (1987) teaches that marigold extract is known for anti-inflammatory activity. There is no mention of marigold extract being used as an anti-psoriatic agent.

Gracza L. Planta Medica 53, page 227 (1987) discloses various oxygen containing terpene derivatives from Calendula Officinalis. The uses of these are indicated for leukorrhoea and trichomonacide activity. There is no mention of using the terpene derivatives as anti-psoriatic agents.

Fazakas B. and Rácz, G. Farmacia Vol. XIII, number 2, page 91 (1965) also teaches that extracts from the flowers of Calendula Officianalis are employed in traditional herbal medicine for leukorrhoea (excessive fluor albus) and showed a good trichomonacide activity.

Gracza L. and Szász K. Acta Pharm. Hung. 38, pp 118–125 (1968) reports on a chemical analysis of the petals of marigold (Calendula Officianalis) with the aim of separating and identifying the solution or solutions which are responsible for the trichomonacide effect reported by Fazakas and Rácz (supra). The most active liquid compounds isolated were described as terpenic alcohols and terpenic lactons according to spectroscopic data.

Jakupovic et al. Planta Medica 54 (3) pp 254–256 (1988) teaches the extraction and isolation of five sesquiterpene glycosides from *Calendula persica*. There is no mention of potential or actual uses for the extracted and isolated molecules.

Ahmed A Ahmed et al., Journal of Natural Products Vol. 56, number 10, pp 1821–1824 (1993) relates to extraction products from *Calendula arvensis*. The products are described as four new sesquiterpene glycosides and three known ones. There is no reference to possible uses therefore.

EP 364442 B1 describes a therapeutic composition against psoriasis comprising an oil extract of at least three herbs selected from a range of herbs which range may include Calendula. However, it is stated that separate extractions of herbs did not provide a curative effect against psoriasis when used singly. Furthermore, it is stated that decoctions of Calendula per se are used for inter alia gastric and intestinal ulcer treatment. Calendula decoctions are not described as being beneficial for the treatment of skin diseases involving abnormal rates of proliferation of skin cells (e.g. hyperproliferation), in diseases such as psoriasis.

DE 3836519 C2 alleges that a pharmaceutical preparation containing freshly cut composite inflorescences of Calendula Officinalis with milking grease as a salve base is useful in treating psoriasis. However, the composition is described as being able to give rise to allergy which can lead to discontinuation of treatment, and there is no indication of, or the identification of, the active component of the composition. There is no indication of cytostatic activity and furthermore it is not apparent which component or mixture of components in the alleged pharmaceutical preparation based on Calendula Officianalis is/are the active component(s). In addition, there does not appear to be any actual evidence which demonstrates that the composition was employed in the treatment of psoriasis.

Co-pending application PCT/GB96/01792 lists a number of compounds useful in the treatment of psoriasis.

There exists a need for the development of new cytostatic drugs which are effective in combatting the onset, maintenance and/or development of disease involving hyperproliferation of dermis cells, in particular for psoriasis treatment.

SUMMARY OF INVENTION

Objects of the invention will become apparent from the following description and examples.

The present invention relates to certain sesquiterpene glycoside stereoisomers useful in the treatment of disease involving hyperproliferation of dermis cells, in particular, psoriasis.

DETAILED DESCRIPTION OF THE INVENTION

According to one aspect of the present invention there is provided use of a compound of general Formula (I):

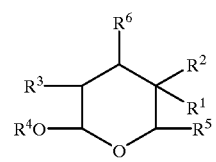

(I)

wherein $R^1$ and $R^2$ are independently selected from H, —OH

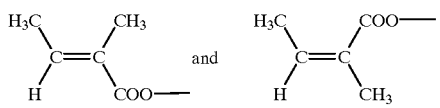

and related esters and ethers thereto;

$R^3$ is selected from —OH,

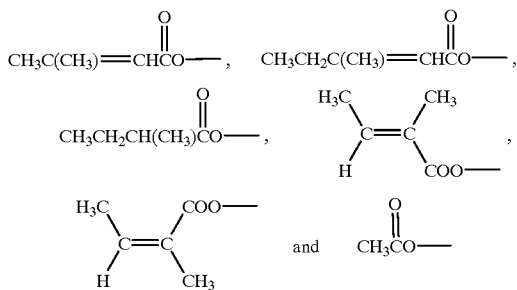

and related esters and ethers thereto;

$R^4$ is

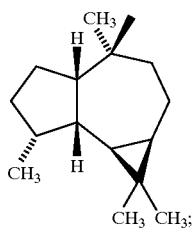

$R^5$ is selected from the group $CH_3$, —CHO, —COOH, —$CH_2OH$ and related esters and ethers thereto; and $R^6$ is selected from OH,

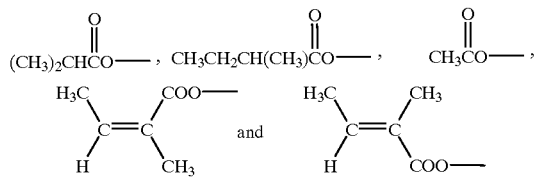

in the preparation of a medicament for the treatment of disease involving hyperproliferation of dermis cells.

For the purposes of the present invention "related esters and ethers" refers to all defined esters of R groups mentioned herein and in general to saturated or unsaturated straight- or branched chain $C_1$–$C_{20}$ carboxy alkyl esterifying acids. Suitable examples include esterifying acids comprising methyl, ethyl, propyl, isopropyl, butyl, isobutyl, sec-butyl, and all isomers of pentanyl, pentenyl, hexanyl and hexenyl alkyl groups. Also included within the term "related esters" are aromatic acids such as benzoic acid and cinnamic acid. $C_1$–$C_{20}$ alkyl ethers comprising straight- or branched-chain alkyl groups as defined for "related esters" above are also encompassed herein.

In a preferred aspect there is provided use of a subset of compounds of Formula (I) as defined above, in the preparation of a medicament for the treatment of disease involving hyperproliferation of dermis cells for example, psoriasis wherein $R^1$ and $R^2$ are independently selected from H and OH ($\beta$OH or $\alpha$OH);

$R^3$ is selected from OH,

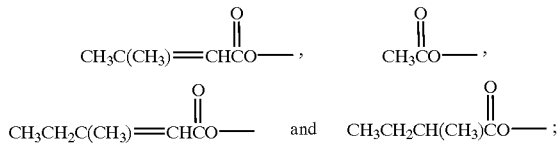

$R^4$ is

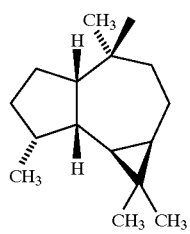

$R^5$ is $CH_3$; and
$R^6$ is selected from OH,

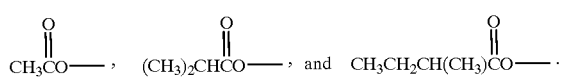

There is also provided use of a compound of Formula (I) extractable from a Calendula species in the preparation of a medicament for the treatment of disease involving hyperproliferation of dermis cells, for example, psoriasis wherein $R^1$ and $R^2$ are independently selected from H and OH ($\beta$OH or $\alpha$OH);

$R^3$ is selected from OH and (E)-3-methylpent-2-enoate i.e.

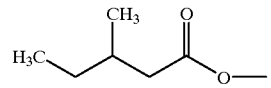

$R^4$ is

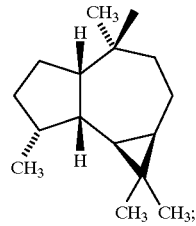

$R^5$ is $CH_3$; and
$R^6$ is OH.

The skilled addressee will also appreciate that groups $R^1$, $R^2$, $R^6$ and $R^3$ may be located in either the axial or equatorial position.

Naturally, the skilled addressee will appreciate that physiologically functional isomers of Formula (I) both those found in Calendula species and synthetically derived isomers therefrom including conformational and constitutional isomers as well as D and L forms of Formula (I) are encompassed by the present invention. Preferably, the fucose component of Formula (I) is D-fucose. Examples of conformational isomers of the invention are encompassed in Formulae (1a) and (1b) as follows:

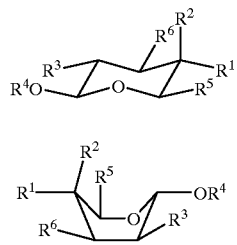

wherein $R^1$, $R^2$, $R^3$, $R^4$, $R^5$ and $R^6$ are as defined for Formula (1). Naturally, the skilled addressee will appreciate that other constitutional isomeric variants relating to "chair" (Formula (Ia)) and "boat" shapes (Formula (Ib)) possessing physiological functionality are permissible within the ambit of the invention. Compounds of Formula (I) can be isolated from Calendula species using conventional organic solvent extraction technology. Generally, compounds of Formula (I) can be extracted from any plant tissue such as leaves, stems, flower parts, roots, shoots and the like.

In a further aspect of the invention novel compounds are provided according to general Formula (I) as first above written. Preferred compounds are those in which $R^1$ and $R^2$ are independently selected from —OH, H

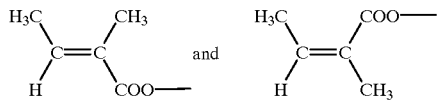

$R^3$ is selected from (E)-3-methylpent-2-enoate and

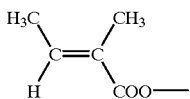

$R^4$ is

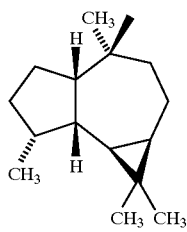

$R^5$ is selected from —CH$_3$, —CHO, —CH$_2$OH and —COOH;

$R^6$ is selected from

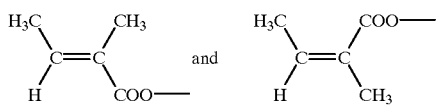

and physiologically functional isomers thereof.

In a preferment there is provided compounds of Formula (I) wherein $R^1$ and $R^2$ are independently selected from H and —OH;

$R^3$ is (E)-3-methylpent-2-enoate;

$R^4$ is

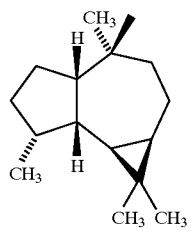

$R^5$ is CH$_3$; and $R^6$ is OH;

and physiologically functional isomers thereof.

The skilled addressee will also appreciate that groups $R^1$, $R^2$, $R^6$ and $R^3$ can be located in either the axial or equatorial position.

"Physiologically functional isomers" for the purposes of the present invention means those isomers which are capable of substantially slowing down or stopping hyperproliferation of dermis cells. Thus, such isomers should be indicated as having a substantially cytostatic effect on dermis cells and as such are indicated as being useful in the treatment of skin diseases such as psoriasis.

Examples or novel compounds according to the invention include:

(i) (rel)-1aα, ra ξ, 7aβ, 7bα-Decahydro-1,1,4ξ, 7α-tetramethyl-1H-cycloprop[e]azulen-4ξ-o-(2-E-{3-methylpent-2-enoyl}-β-quinovopyranoside (Van-10-3).

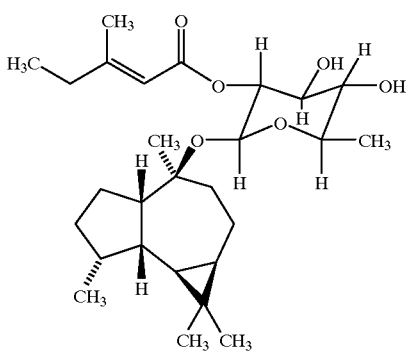

(ii) (rel)-1α, 4aξ, 7aβ, 7bα-Decahydro-1,1,4ξ, 7α-tetramethyl-1H-cycloprop[e]azulen-4ξ-o-(2-E-{3-methyl}pent-2-enoyl)-β-fucopyranoside (Van-10-4).

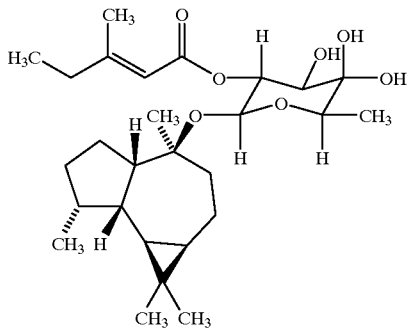

A preferred novel compound of the invention on the basis of its biological activity is (ii) above, and physiologically functional derivatives and analogues thereof.

Included as an embodiment of the invention is use of compounds of Formula (I) in a composition for the treatment of disease involving hyperproliferation of dermis cells, in particular for the treatment of psoriasis. Naturally, the skilled addressee will appreciate that such a use can include the use of known compounds isolated from Calendula species such as, (iii) (rel)-1α, 4aξ, 7aβ, 7bα-Decahydro-1,1,4ξ, 7α-tetramethyl-1H-cycloprop[e]azulen-4ξ-o-β-fucopyranoside (Van 15A).

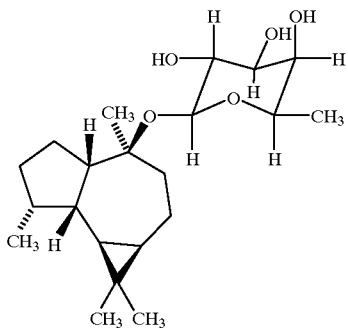

A preferred compound used in the preparation of a medicament for the treatment of a skin disorder such as psoriasis, is compound (ii) above.

In a further aspect of the invention there is provided a compound of Formula (I), particularly a compound selected from (i), (ii) and (iii) for use as a medicament. The definition of $R^1$, $R^2$, $R^3$, $R^4$, $R^5$ and $R^6$ of Formula (I) are as given hereinabove.

The skilled addressee will appreciate that analogues of compounds (i) to (iii) above may be synthesised therefrom in situ. For example where groups $R^1$ and $R^6$ are both OH, or $R^2$ and $R^6$ are both —OH, they may be esterified to the angelate, tiglate or other ester by reaction of the appropriate acid chloride or acid anhydride with appropriate start compound, for example compound (ii), in the presence of a suitable base such as pyridine. Both OH groups will be esterified by this technique. Derivatives with different ester groups on $R^1$ and $R^6$ e.g. tiglate and angelate may also be prepared by reacting suitable compounds such as compound (ii) with a mixture of two acid chlorides or two anhydrides. This will produce all four possible isomers which can then be separated using standard techniques such as chromatography an silica gel and the like.

The ethyl crotonate arm ($R^3$) on compounds (i) and (ii) can be replaced by other carboxylic acid esters using the following general procedure. The $R^1$ and $R^6$ hydroxyl functions can be protected by the formation of the acetonide by reaction of the compound with acetone in the presence of toluene sulphonic acid or by similar techniques known in the art such as those described in Protective Groups in Organic Synthesis, Second Edition, T. W. Greene, P. G. M. Wuts (ISBN 0 471 62301 6) (e.g. Chapter 2, pp 123–127) herein incorporated by reference, producing for example, a compound such as compound A below or similar compounds.

(A)

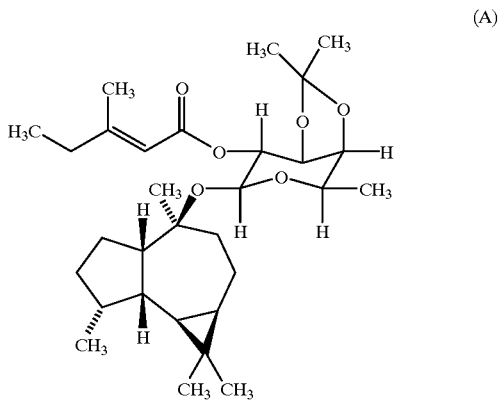

The ethyl crotonate arm can be removed by acid or base hydrolysis of for example, compound (ii), to yield product with $R^3$=OH. The resulting compound can then be reacted with an appropriate acid chloride or acid anhydride in the presence of a base such as pyridine to yield an ester such as tiglate or angelate on $R^3$. Alternatively such an ester may be formed by trans-esterification of compound A (above) with an excess of organic acid such as tiglic or angelic acids in the presence of a suitable acid or basic catalyst. Finally, the protective acetonide group, can be cleaved by suitable cleaving reagents such as iodine in methanol such as described in Greene T. W. (supra).

Also encompassed within the ambit of the invention is a therapeutic composition against psoriasis characterised in that it contains at least one sesquiterpene glycoside of Formula (I). The sesquiterpene glycoside may be at least one selected from, for example, compounds (i), (ii) and (iii). Preferably the at least one sesquiterpene glycoside is compound (ii). Naturally, the skilled addressee will appreciate that such compositions may comprise two or more plant glycosides of Formula (I) in any concentration which is capable of giving rise to a therapeutic cytostatic effect. Thus, therapeutic compositions can comprise plant extracts of Calendula substantially devoid of undesirable contaminating compounds. The plant extracts may have, for example, undergone a number of solvent extraction steps substantially to separate out undesirable components from desirable components such as those encompassed by Formula (I). Naturally, plant extracts which have undergone such solvent extraction steps can contain more than one plant glycoside and may contain several plant glycosides. Such plant extracts may then be subjected to further solvent extraction procedures to isolate individual active plant glycoside compounds of Formula (I).

There now follows a description of a general method of obtaining purified extracts of Calendula species containing active components capable of producing a cytostatic effect on dermis cells, the refinement of such extracts, and the isolation of active components from extracts and/or subsequent purification thereof.

Flowers of a Calendula species are pulverised in a grinder and the resulting powder soxhlet-extracted with petroleum ether until exhaustion. The extract can then be concentrated, for example, under reduced pressure using an evaporator, such as a rotary evaporator to provide an extract residue, the crude extract. The crude extract can then be fractionated via, for example, vacuum liquid chromatography (VLC) using suitable solvents and solvent systems of increasing polarity. Suitable solvents include solvents such as polar and non-polar organic solvents and mixtures thereof. Examples of solvents which may be used in an extraction method suitable for the purposes of the present invention include the following (volume ratios).
Petrol-EtOAc (EtOAc 0–10%) Petrol-EtOAc (EtOAc 12–18%) Petrol-EtOAc (EtOAc 20–24%) Petrol-EtOAc (EtOAc 24–30%) Petrol-EtOAc (EtOAc 35–40%) Petrol-EtOAc (EtOAc 45%) Petrol EtOAc (EtOAc 50–55%) Petrol-EtOAc (EtOAc 60%) Petrol-EtOAc (EtOAc 65–75%) Petrol-EtOAc (EtOAc 80–85%) Petrol-EtOAc (EtOAc 90–95%) Petrol-EtOAc (EtOAc 95%) Petrol-MeOH (MeOH 0–5%) EtOAc-MeOH (MeOH 10–100%) hexane, hexane:chloroform mixtures in volume ratios such as:

| Hexane:Chloroform |
| --- |
| 100:0 |
| 95:5 |
| 9:1 |
| 8:2 |
| 6:4 |
| 4:6 |
| 0:100 | chloroform, and chloroform: methanol mixtures (e.g. 5:1; 1:1) and the like. Thus, the crude extract can undergo fractionation several times using different mixtures of organic solvents in pre-selected ratios of, for example, increasing polarity.

Under VLC, silica gel (Merck 7749) is typically packed into a receptacle, for example a sintered funnel under applied vacuum, to give a column. The crude extract can be readied for introduction to the VLC column by for example, adsorption on silica (for example, 1:1 weight/weight) and placed on top of the column as described above, and eluted at least once with a solvent or a solvent system of increasing polarity, such as those mentioned herein in pre-specified rations. Eluants from the VLC column are collected and can be subjected to further fractionation steps via column chromatography or other suitable chromatographical means. After fractionation of the crude extract, collected eluants can be subjected to preparative thin layer chromatography (TLC) for analysis of active constituents contained therein. For example, in one method an eluent fraction designated Van-5-10, obtained from column chromatography utilising a chloroform: methanol mix ratio of 95:5 is subjected to TLC analysis using an initial solvent system of hexane: chloroform: ethyl acetate in a volume ratio of 3:6:6, giving five fractions, designated Van-9-1, Van-9-2, Van-9-3, van-9-4 and Van-9-5. Such fractions can be regarded as comprising purified mixtures of distinct glycosidic molecules encompassed by Formula (I) and are therefore able to be viewed as mixtures substantially free of contaminating components such as plant proteins, plant hormones and the like. Such eluent fractions possessing cytostatic activity form an embodiment of the present invention.

In a further step, fractions Van-9-1 to Van-9-5 as mentioned hereinabove can be subjected to further preparative thin layer chromatography (prep. TLC) silica gel analyses using further organic solvent preparations. For example, eluent fraction Van-9-2 can be subjected to prep. TLC utilising as a solvent preparation hexane: chloroform: ethyl acetate at a ratio of 3:6:4, giving sub-fractions of Van-9-2, designated Van-9-2B and Van-9-2C. Sub-fractions resulting from the prep. TLC step can be subjected to further chromatographical steps such as high pressure liquid chromatography (HPLC). For example, TLC isolated fractions of Van-9-2-B and Van-9-2-C are subjected to HPLC using an octadecyl-silanol (ODS) (analytical) column with a solvent of 75% acetonitrile in water containing 0.1% Trifluoro acetic acid (TFA). Individual fractions obtained by HPLC techniques may then be assessed for the active component both by using NMR techniques and by analysing such fractions for cytostatic activity in vitro.

For larger batches of raw material, such as dried petals of Calendula Officianalis, the following general method of extraction can be used.

Dried plant material, for example, petals of Calendula Officinalis can be milled to a coarse powder and extracted in a suitable organic solvent. Generally, the extraction method may be any suitable extraction method known in the art, such as soxhlet extraction, batch extraction, and continuous extraction. Thus, as a further aspect of the invention there is provided anti-psoriatic compounds of Formula (I) obtainable from a Calendula species particularly by way of a soxhlet, batch or continuous extraction process. Such extraction processes are known in the art. Preferably the Calendula species is Calendula Officinalis and the preferred extraction method is a continuous extraction method. Suitable organic solvents for use in a continuous extraction method include polar and non-polar organic solvents such as methanol, ethanol, dichloromethane, toluene, hexane, ethyl acetate, isopropyl like. Preferably, the solvent is a non-polar organic solvent such as heptane. The resulting extract is concentrated under vacuum until an appropriate weight of extract/total volume of solution percentage ratio (% w/v) is obtained. A suitable % w/v to 60% w/v, more preferably between 15 w/v and 30% w/v and most preferably around 20% w/v. The resulting concentrate is further extracted in a polar solvent/water solution at a suitable parts by weight: parts by weight ratio such as 10:0 to 7:3. Preferably the ratio is from 10:0 to 8:2. More preferably the ratio is 9:1. A suitable polar organic solvent may be selected from acetonitrile, methanol, ethanol, ethyl acetate and the like. A preferred polar organic solvent is acetonitrile. The heptane fraction is discarded and the VAN- containing polar organic solvent fractions (such as acetonitrile fractions) can then be combined and the polar organic solvent removed under vacuum. The resulting solid can then be redissolved in a suitable polar or non-polar organic solvent such as ethyl acetate, methanol, acetonitrile, diethyl ether, dichloromethane, toluene and the like, and then washed successively with a base such as sodium bicarbonate in a 10:30% w/v ratio, water, dilute, inorganic acid such as hydrochloric acid at a concentration of from 0.05 to 0.1 M or dilute organic acids such as citric acid at a concentration of from 0.2 M to 1.0 M, and finally water. The organic solvent solution is then evaporated off under vacuum.

The resulting crude preparation may be further purified to an appropriate VAN-10 compound, such as VAN-10-4 (compound (ii) above). The crude preparation may be re-dissolved in a suitable volume of organic solvent such as a polar organic solvent or a suitable volume of a mixture of at least one polar organic solvent: at least one non-polar organic solvent. Preferably, the organic solvent consists of one polar organic solvent in admixture with one non-polar organic solvent. Where a suitable mixture of organic solvents is employed, they should be miscible within one another. The % ratio (w/v) of polar organic solvent: non-polar organic solvent can lie between 80:20 and 20:80% (w/v) preferably 30:70 and 70:30 % (w/v). For example, an amount of the crude extract can be re-dissolved in a suitable volume of polar organic solvent: non-polar organic solvent at a percentage ratio of 50% polar organic solvent: 50% non-polar organic solvent ratio. A preferred solvent mixture is 50% ethyl acetate: 50% hexane. Further suitable solvent may be selected from polar and non-polar organic solvents as described above. The dissolved material may be loaded onto a flash chromatography system, such as a flash column and eluted at a suitable flow rate using a suitable solvent mixture as the mobile phase e.g. 50% ethyl acetate: 50% hexane. A suitable flow rate from a flash chromatography column can be from 50–500 mls/min depending on the size of column used, preferably from 100–250 mls/min, more preferably about 250 mls/min using, for example, a 50% ethyl acetate: 50% hexane mixture as the mobile phase. The ratio of polar solvent: non-polar solvent for the mobile phase can lie within the ranges used to re-dissolve the crude extract as outline above. The actual ratio will depend on the solvent mixes employed. Using the flash system described the VAN mixture may be isolated into a number of fractions. These fractions may then be combined and evaporated to dryness. After evaporation the combined fractions (i.e. semi crude material) can be re-dissolved in a suitable polar organic solvent, such as those polar solvents mentioned above and samples of the dissolved fractions purified, for example, by HPLC using a reverse-phase column such as a spherisorb column or the like. A stock solution of the resulting combined (semi-crude) material obtained after flash chromatography but before HPLC can be re-dissolved in a solvent similar to that used as the mobile phase and divided up into aliquots. The aliquots may be then be processed by standard HPLC techniques known in the art, such as by isocratic separation or by gradient elution. Naturally, the man skilled in the art will appreciate that the maximum concentration of semi-crude re-dissolved in the mobile phase may be dependent on the solvent employed. For example, up to 25 mg/ml or combined (semi-crude) extract can be re-dissolved in acetonitrile which may then be divided into suitable volumes for running on an HPLC column. Each sample is run for a period of time depending on the mobile phase employed and VAN-10 compounds can be eluted at appropriate time intervals. Suitable time intervals may be worked out by making preliminary HPLC runs on an analytical column using different solvent systems as the mobile phase and selecting a solvent system which results in an optimum speed of elution and good resolution of the sample. In the mobile phase the % polar organic solvent: % non-organic polar solvent may lie in the range 90:10 to 10:90, preferably from 70–80: 30:20, most preferably from 75–80: 25–20. Thus, for HPLC purification, a mobile phase consisting of acetonitrile: water can be 75% acetonitrile: 25% water and the flow rate can be set according to the size of column used, such as 5 ml/per min. Suitable polar organic solvents include those mentioned above. Preferred organic solvents are acetonitrile or methanol.

It will be apparent to the skilled addressee that the selection of solvent, or mixtures of solvents for each step in the isolation of active principles can be guided by results of bioassay analysis of separate fractions, and ultimately, the identification of active components found in the separate fractions, at different steps of the extraction procedure.

Compounds of the present invention have been found to possess cytostatic activity in mouse embryonic fibroblast cells in vitro. Thus, cytostatic activity of compounds of general Formula (I) has been demonstrated in a number of tests for cytostasis in vitro. Furthermore, cytostatic activity of compounds of general Formula (I) has been demonstrated in vivo.

The compounds of the present invention are indicated as being useful for the treatment of skin diseases wherein abnormally high cell proliferation is observed in the disease process. They may be employed in treating skin disease disorders, such as psoriasis, wherein abnormally high cell proliferation is a recognised symptom of said skin disorders.

The invention thus further provides a method for the treatment of skin disorders such as psoriasis in mammals, including humans, which comprises the use of a clinically useful amount of compound of Formula (I) or physiologically functional derivative in a pharmaceutically useful form, once or several times a day or in any other appropriate schedule for example, orally, or applied topically.

In addition, there is provided as a further, or alternative, aspect of the invention, a compound of Formula (I) or physiologically functional derivative thereof for use in therapy, for example psoriasis and the like.

The amount of compound of Formula (I) required to be effective as a cytostatic agent will, of course, vary and is ultimately at the discretion of the medical or veterinary practitioner. The factors to be considered include the condition being treated, the route of administration, and nature of the formulation, the mammal's body weight, surface area, age and general condition and the particular compound to be administered. A suitable effective dose of cytostatic compounds of the invention generally lies in the range of about 0.01 to about 120 mg/kg bodyweight, e.g. 0.1 to about 120 mg/kg body weight, preferably in the range of about 0.1 to 50 mg/kg, for example 0.5 to 50 mg/kg. The total daily dose may be given as a single dose, multiple doses, e.g. two to six times applications per day. For example, for a 75 kg mammal (e.g. a human) the dose range would be about 8 to 9000 mg per day, and a typical dose could be about 50 mg per day. If discrete multiple doses are indicated treatment might typically be 15 mg of a compound of Formula (I) given up to 4 times per day.

Whilst it is possible for the active compound to be administered alone, it is preferred to present the active compound in a pharmaceutical formulation. Formulations of the present invention, for medical use, comprise a compound of Formula (I) together with one or more pharmaceutically acceptable carriers and optionally other therapeutic ingredients. The carrier(s) should be pharmaceutically acceptable in the sense of being compatible with the other ingredients of the formulation and substantially non-deleterious to the recipient thereof.

The present invention, therefore, further provides a pharmaceutical formulation comprising a compound of Formula (I) or physiologically functional derivative thereof together with a pharmaceutically acceptable carrier therefore. In a preferment the pharmaceutical formulation comprises a compound selected from compounds (i), (ii) and (iii), especially compound (ii).

Naturally, the skilled addressee will appreciate that any pharmaceutical formulation comprising an active compound of Formula (I) can include at least one active compound isolated and/or purified from an extract derived from a Calendula species. Preferably, the Calendula species is selected from at least one of Calendula Officianalis, *Calendula arvensis*, and Calendula persica. Most preferably the active compound isolated from a Calendula species is isolated and/or purified from *Calendula officinalis*. Thus a pharmaceutical formulation may contain an active component isolated and/or purified from two or more Calendula species, which active component can be made up of two or more active compounds encompassed by Formula (I) above, such as compounds (i) and (ii).

In a further embodiment, a pharmaceutical formulation may comprise a mixture of at least one active compound isolated and/or purified from an extract derived from Calendula officinalis, and at least one active compound isolated and/or purified from *Calendula arvensis* or *Calendula persica* of Formula (I).

There is also provided a method for the preparation of a pharmaceutical formulation comprising bringing into association a compound of Formula (I) or physiologically functional derivative thereof, and a pharmaceutically acceptable carrier therefore.

Formulations according to the present invention include those suitable for oral or topical administration. Preferred formulations are those suitable for topical administration, such as to the skin. For infections of external tissues, e.g. skin, the formulations are preferably applied as a topical ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

Topical formulations including at least one compound of Formula (I) may also be administered in the form of suitable liposomal or niosomal preparations, and/or in cyclodextrin-based formulations.

If desired, the aqueous phase of the cream may include, for example, at least 30% w/w of a polyhydric alcohol, i.e. an alcohol having two or more hydroxyl groups such as propylene glycol, butane-1,3-diol, mannitol, sorbitol, glyercol and polyethylene glycol and mixtures thereof. The topical formations may desirably include a compound which enhances absorption or penetration of the active ingredient through the skin or other affected areas. Examples of such dermal penetration enhancers include dimethylsulphoxide and related analogues.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glycerol monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol cAP may be used, the last three being preferred esters. These may be used alone or in combination depending on the properties required. Alternatively, high melting point lipids such as white soft paraffin and/or liquid paraffin or other mineral oils can be used.

The formulations may conveniently be presented in unit dosage form and may be prepared by any of the methods well known in the art of pharmacy. All methods include the step of bringing the active compound(s) into association with a carrier which constitutes one or more accessory ingredients. In general, the formulations are prepared by uniformly and intimately bringing the active compound(s) into association with a liquid carrier or a finely divided solid carrier or both and then, if necessary, shaping the product into desired formulations.

Formulations of the present invention suitable for oral administration may be presented as discrete units such as capsules, sachets, tablets, lozenges, comprising the active ingredient in a flavoured based, usually sucrose and acacia or tragacanth; pastilles comprising the active ingredient in an inert base such as gelatin and glycerin, or sucrose and acacia; and mouth-washes comprising the active ingredient in a suitable liquid carrier. Each formulation generally contains a predetermined amount of the active compound; as a powder or granules; or a solution or suspension in an aqueous or non-aqueous liquid such as a syrup, an elixir, an emulsion or draught and the like.

A tablet may be made by compression or moulding optionally with one or more accessory ingredients. Compressed tablets may be prepared by compressing an a suitable machine the active compound in a free-flowing form such as a powder or granules, optionally mixed with a binder, (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide the desired release profile.

A syrup may be made by adding the active compound to a concentrated, aqueous solution of a sugar, for example sucrose, to which may also be added any necessary ingredients. Such accessory ingredient(s) may include flavourings, an agent to retard crystallisation of the sugar or an agent to increase the solubility of any other ingredients, such as a polyhydric alcohol for example glycerol or sorbitol.

In addition to the aforementioned ingredients, the formulations of this invention may further include on or more accessory ingredients) selected from diluents, buffers, flavouring agents, binders, surface active agents, thickeners, lubricants, preservatives (including antioxidants) and the like.

In a further aspect the present invention provides the use of a compound of Formula (I) or physiologically functional derivative thereof for the manufacture of a medicament for the treatment of psoriasis.

Figure 2:
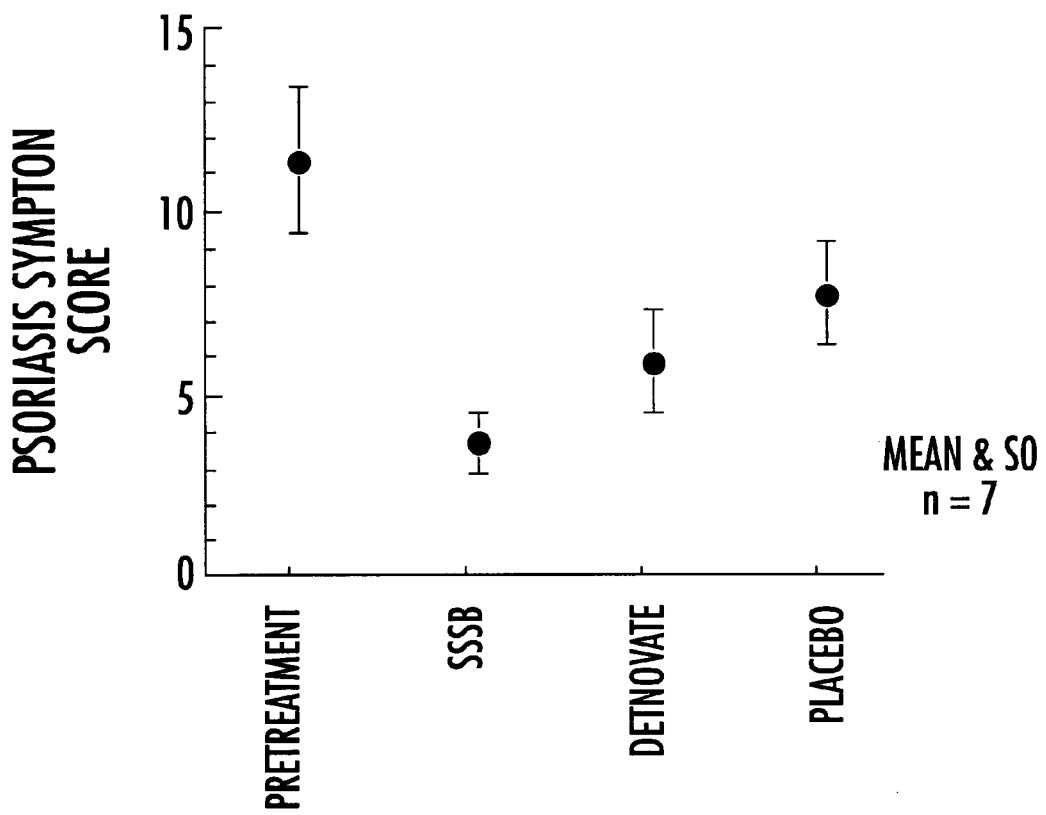
Figure 1:
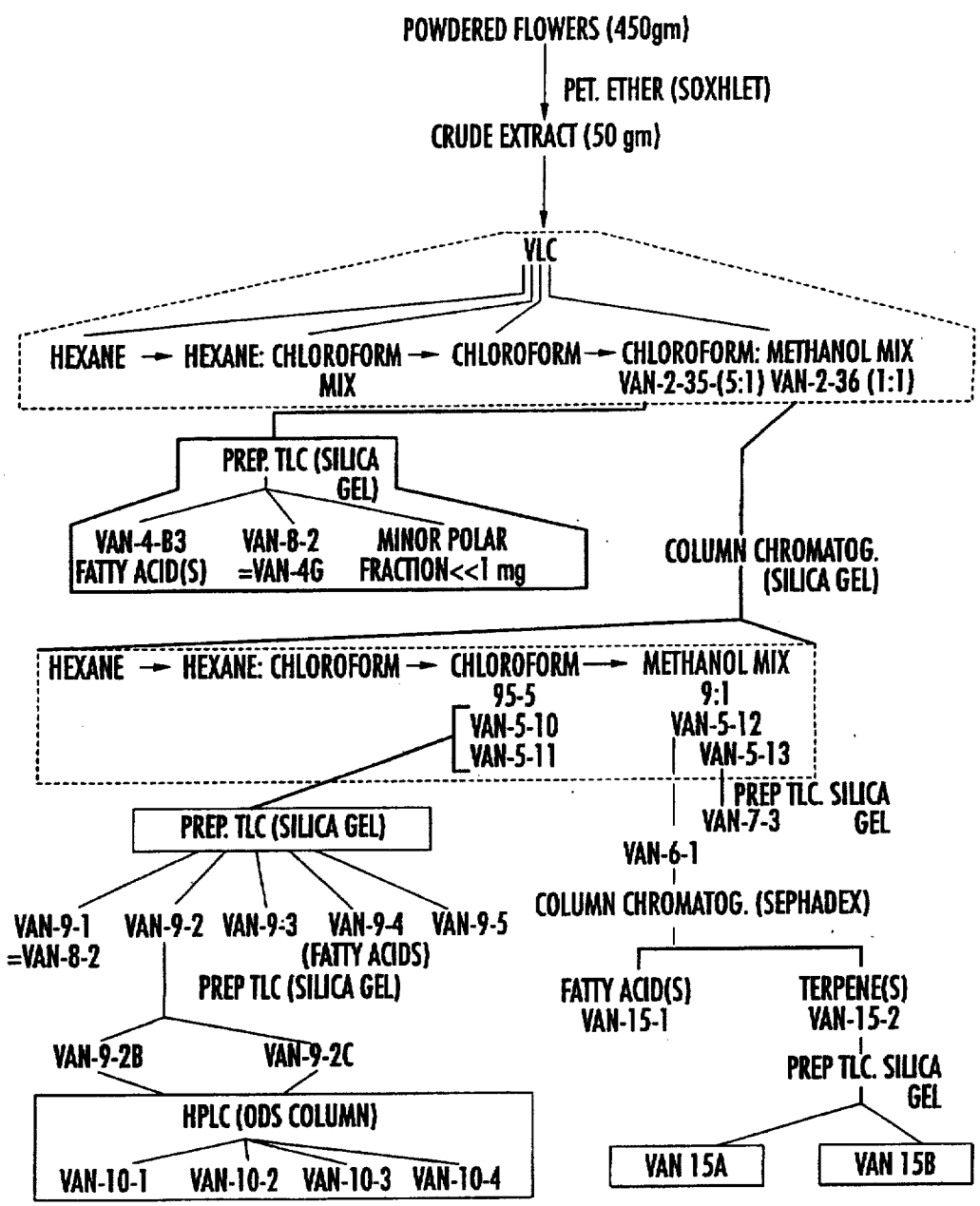
Figure 2:
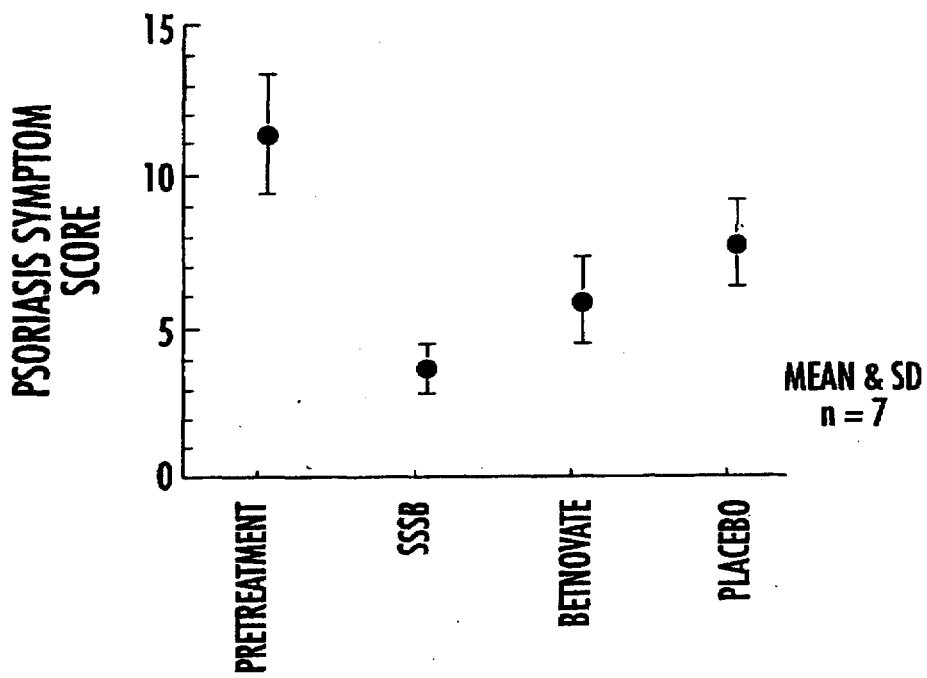

FIG. 1: Schematic diagram showing extraction steps for isolating cytostatic compounds of Formula (I) from flowers of Calendula officianalis;

FIG. 2: Results of treating patients suffering from psoriasis with extract of Calendula officianalis.

The invention will now be illustrated by the following non-limiting Examples.

EXAMPLE 1

Isolation of Extract VAN-6-1

Reference is made to FIG. 1.

Extraction and Fractionation of the Plant Material 400 g of powdered plant material was soxhlet-extracted with petroleum ether (60–80°) until exhaustion. The extract was then concentrated under reduced pressure using a rotary evaporator to give 49 g of extract residue. The plant material was further extracted with chloroform under similar conditions as described above to give a further extract. These crude extracts were then fractionated using vacuum liquid chromatography (VLC). Silica gel (Merk 7749) was packed into a sintered funnel under applied vacuum to give a column of about 10 cm in diameter and 5 cm in height. The extract (20 g at a time) absorbed in silica (1:1 w/w was then placed on top of the column and eluted with solvents of increasing polarity; i.e. hexane, hexane containing increasing concentrations of chloroform, chloroform and chloroform containing increasing amounts of methanol. VLC eluants were collected and fractions analysed by TLC for their constituents. Based on the TLC analysis, VLC eluants were pooled giving thirteen fractions (Table 1). These were tested for their cell growth inhibitory activity, following the 3T3 bioassay procedure (Example 5).

An eluent, designated VAN-2-26 (extracted using a 1:1 mixture of chloroform and methanol) was found to be most active.

TABLE 1

| Fraction | Solvent System |
|---|---|
| VAN-2-1 | Hexane |
| VAN-2-2 | Hexane |
| VAN-2-6 | Hexane: Chloroform (95:5) |
| VAN-2-12 | Hexane: Chloroform (8:2) |
| VAN-2-15 | Hexane: Chloroform (6:4) |
| VAN-2-21 | Hexane: Chloroform (6:4) |
| VAN-2-23 | Hexane: Chloroform (6:4) |
| VAN-2-25 | Hexane: Chloroform (4:6) |
| VAN-2-27 | Hexane: Chloroform (4:6) |
| VAN-2-31 | Chloroform |
| VAN-2-35 | Chloroform: Methanol (5:1) |
| VAN-2-26 | Chloroform: Methanol (1.1) |
| VAN-3-37 | Chloroform: Methanol (1.1) |

Eluent VAN-2-36 was subjected to column chromatography over silica gel with hexane: chloroform and chloroform: methanol mixtures of increasing polarity. The fractions eluted with 10–60% chloroform (in hexane) gave VAN-5-4 while those fractions eluted with 5% methanol (in chloroform (in hexane)) gave VAN-5-4 while those fractions eluted with 5% methanol (in chloroform) gave VAN-5-9. Both of these fractions appeared to be mixtures of fatty acids (from GC and NMR spectra) and showed no cell growth inhibition. VAN-5-10 was located in a 5% methanol eluate while VAN-5-11, VAN-5-12 and VAN-5-15 were fractions obtained from the 10% methanol eluates.

Further attempt to purify VAN-5-12 was made using prep. TLC (silica gel, solvent-chloroform: methanol; 95.5). This gave VAN-6-1 which was found to be very active using the cell growth bio assay (Example 5).

EXAMPLE 2

Isolation of VAN-9-2

The procedure of Example 1 (above) was followed up to and including the VLC and TLC analysis.

VAN-5-10 was subjected to preparative TLC (silica gel; solvent; hexane; chloroform; ethyl acetate, 3:6:6) to give five fractions, VAN-9-1 to VAN-9-5, of which VAN-9-2 was found to be biologically active using the 3T3 cell bioassay (Example 5).

EXAMPLE 3

Isolation of VAN-10-3 and VAN-10-4

The protocols of Examples 1 and 2 above were followed to reach VAN-9-2.

VAN-9-2 was separated into VAN-9-2B and VAN-9-2C by preparative TLC (solvent: hexane: chloroform: ethyl acetate, 3:6:4).

VAN-9-2B and VAN-9-2C were separated by HPLC on an ODS analytical column using 75% acetonitrile in water (plus 0.1% trifluoroacetic acid). This gave four fractions, VAN-10-1, VAN-10-2, VAN-10-3, and VAN-10-4. NMR data for VAN-10-3 and VAN-10-4 is provided hereinbelow.

It is believed that the stereochemistry of VAN compounds at the aromadendranol moiety is the following structure:

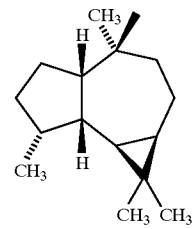

| | $^1H$ | | $^{13}C$ |
|---|---|---|---|
| Carbon/Proton | $\delta_h$ (J in Hz) | Multiplicities* | $\delta_c$ |
| 1 | 0.65 m | C | 19.4 |
| 1a | | CH | 29.7 |
| 2 | | $CH_2$ | 19.4 |
| 3 | | $CH_2$ | 39.3 |
| 4 | | C | 81.7 |
| 4a | | CH | 55.2 |
| 6 | | $CH_2$ | 26.2 |
| 6 | | $CH_2$ | 29.7 |
| 7 | | CH | 39.1 |
| 7a | 1.85 m | CH | 40.4 |
| 7b | 0.10 t (9.4) | CH | 23.1 |
| 8 | 0.95 s | Me | 17.1 |
| 9 | 1.00 s | Me | 29.3 |
| 10 | 1.35 s | Me | 27.0 |
| 11 | 0.90 s | Me | 17.2 |
| 1' | 5.0 hidden | CH | 96.0 |
| 2' | 5.55 t (8.3) | CH | 77.6 |
| 3' | 4.25 dd (8.3) | CH | 77.1 |
| 4' | 3.7 t (8) | CH | 75.0 |
| 5' | 3.75 t (8) | CH | 73.0 |
| 6' | 1.56 d (7) | Me | 19.4 |
| 1" | | C | 166.4 |
| 2" | 5.85 br s | CH | 115.8 |
| 3" | | C | 162.0 |

-continued

| | ¹H | | ¹³C | |
|---|---|---|---|---|
| Carbon/Proton | δ_h (J in Hz) | Multiplicities* | δ_c | |
| 4" | 2.05 m | CH₂ | 34.3 | |
| 5" | 0.95 t (7) | Me | 12.2 | |
| 6" | 2.25 br s | Me | 17.0 | |

*Obtained from the J-mod. experiment
¹H and ¹³C-NMR chemical shift data (pyridine-D₅) for Van-10-3

| | ¹H | | ¹³C | |
|---|---|---|---|---|
| Carbon/Proton | (δ_h (J in Hz) | Multiplicities* | δ_c | |
| 1 | | C | 19.4 | |
| 1a | 0.62 m | CH | 29.7 | |
| 2 | 1.55, 1.8 m | CH₂ | 19.2 | |
| 3 | | CH₂ | 39.3 | |
| 4 | | C | 81.5 | |
| 4a | | CH | 55.2 | |
| 6 | | CH₂ | 26.3 | |
| 6 | | CH₂ | 29.7 | |
| 7 | | CH | 39.3 | |
| 7a | 1.85 m | CH | 40.4 | |
| 7b | 0.10 t (9.4) | CH | 23.1 | |
| 8 | 1.10 s | Me | 17.1 | |
| 9 | 1.15 s | Me | 29.8 | |
| 10 | 1.35 s | Me | 27.1 | |
| 11 | 0.95 d (7) | Me | 17.2 | |
| 1' | 4.9 d (7.9) | CH | 96.3 | |
| 2' | 5.85 t (7.9) | CH | 74.4 | |
| 3' | 4.15 dd (7.9, 3.5) | CH | 73.5 | |
| 4' | 4.05 d (3.5) | CH | 73.3 | |
| 5' | 3.85 m | CH | 71.4 | |
| 6' | 1.60 d (6) | Me | 17.9 | |
| 1" | | C | 166.6 | |
| 2" | 5.85 br s | CH | 115.9 | |
| 3" | | C | 161.7 | |
| 4" | 2.05 m | CH₂ | 34.3 | |
| 5" | 0.95 t (7) | Me | 12.2 | |
| 6" | 2.22 br s | Me | 19.3 | |

*Obtained from the J-mod. and HC-COEI experiments.
¹H and ¹³C-NMR chemical shift data (pyridine-D₅) for Van-10-4

EXAMPLE 4

Isolation of VAN-15A

Reference is made to FIG. 1.

The protocols of Examples 1 and 2 were followed to get to VAN-6-1.

VAN-6-1 was fractionated by column chromatography (Sephadex LH20: solvent: chloroform: methanol, 1:1) into two fractions: VAN-15-1 (heavier fraction containing fatty acids) and VAN-15-2 (lighter fraction containing terpenes).

VAN-15-2, was subjected to preparative TLC (silica gel; solvent: chloroform: methanol 95:5) to give VAN-15A and a minor component VAN-15B. NMR data for the active component, VAN-15A is provided hereinbelow.

| | ¹H | | ¹³C | |
|---|---|---|---|---|
| Carbon/Proton | δ_h (J in Hz) | Multiplicities* | δ_c | |
| 1 | | C | 19.4 | |
| 1a | 0.6 br q (9) | CH | 29.7 | |
| 2 | | CH₂ | 19.2 | |
| 3 | | CH₂ | 39.3 | |
| 4 | | C | 81.5 | |
| 4a | | CH | 55.2 | |
| 6 | | CH₂ | 26.3 | |
| 6 | | CH₂ | 29.7 | |
| 7 | | CH | 39.3 | |
| 7a | 1.85 m | CH | 40.4 | |
| 7b | 0.10 t (9.4) | CH | 23.1 | |
| 8 | 0.95 s | Me | 17.1 | |
| 9 | 1.00 s | Me | 29.8 | |
| 10 | 1.35 s | Me | 27.1 | |
| 11 | 0.90 d (7) | Me | 17.2 | |
| 1' | 4.4 d (7.3) | CH | 96.3 | |
| 2' | 3.56 | CH | 74.4 | |
| 3' | 3.56 | CH | 73.5 | |
| 4' | 3.69 d (2.6) | CH | 73.3 | |
| 5' | 3.56 | CH | 71.4 | |
| 6' | 1.25 d (6.0) | Me | 17.9 | |

*Obtained from the J-mod. and HC-COE1 experiments.
¹H and ¹³C-NMR chemical shift data (CDCl₃) for Van-15A

EXAMPLE 5

Reversible Inhibition of Proliferation of Fibroblast-Cell Line 3T3.

Mouse embryonic fibroblast cells (3T3-available from Flow) were plated out on a 96-well tissue culture plate. Cells were suspended in medium (Dulbeco's Modification of Eagles Medium (DMEM), Gibco) containing 10% Foetal Calf Serum (Gibco); 1% Glutamine (Gibco); 1% Penicillin/streptomycin (Gibco); 1% non-essential amino acids (Gibco), at a concentration of 50,000 cells per ml. 100 μl of the cell suspension was pipetted into each well to give a concentration of 5000 cells per well. The cells were incubated for 24 hours at 37° C. in 5% $CO_2$ atmosphere. The medium was removed from the plate and varying dilutions of compounds (0, 30, 45, 60, 100 μg/ml), internally designated, VAN-10-4, VAN-10-2, VAN-10-3 and VAN-15A were prepared by dissolving the compounds in 100% DMSO (Sigma). This was then diluted with DMEM to give a DMSO concentration of 0.5%. The compounds were then diluted to the indicated concentrations (above) with OMEM containing 0.5% DMSO (Sigma) and added to the plate (100 μl/well). Each dilution was done in triplicate; the control was DMEM containing 0.5% DMSO. 50 μl of DMEM containing 0.5 μCi ³H-thymidine was added to each well. Next, 50 μl DMEM containing 40% foetal calf serum (Gibco); 4% penicillin/streptomycin (Gibco); 4% glutamine (Gibco); 4% non-essential amino acids (Gibco) was added to each well. The plates were incubated for 24 hours at 37 °C. in a 5% $CO_2$ atmosphere. The medium including compounds under test was then removed and the plates washed twice (2x) with phosphate buffered saline (PBS) (pH 7.3).

100 μl of 5% trypsin (Gibco) in Versene, (an EDTA chelating agent available from Gibco) was added to each well. The plate was further incubated for 15 minutes at 37° C. in a 5% $CO_2$ atmosphere, then the cells were harvested from the well using a semi-automatic cell harvester (Skatron). Harvested cells were placed in a scintillation vial containing 4 ml of Optiphase "safe" (LKB) and radio activity was counted using a liquid scintillation counter (LKB WALLAC 1217 Rackbeta). Results are shown in Table 2.

TABLE 2

|  | 0 µg/ml | | 15 µg/ml | | 22–5 µg/ml | | 30 µg/ml | | 50 µg/ml | |
| --- | --- | --- | --- | --- | --- | --- | --- | --- | --- | --- |
|  | Mean | SD | Mean | SD | Mean | SD | Mean | SD | Mean | SD |
| VAN 6-1 | 5537.1 | 186.1 | 3947.6 | 454.6 | 3370.5 | 772.8 | 2667.5 | 475.4 | 614.1 | 122.2 |
| VAN 9-2H | 4512.1 | 125 | 859.5 | 168 | 254.5 | 134 | 84.5 | 8 | 40.0 | 8 |
| VAN 9-2C | 4579.5 | 155 | 3759.8 | 301.9 | 1475.6 | 24 | 687.5 | 39 | 188.6 | 27 |
| VAN 10-4 | 4475.1 | 393 | 633.6 | 45 | 111.1 | 19.2 | 88.6 | 17 | 34.5 | 16 |
| VAN 10-2 | 2939.1 | 444 | 925.3 | 651 | 247.0 | 19 | 60.6 | 11 | 24.8 | 10 |
| VAN 10-3 | 2742.8 | 175 | 1887.3 | 432 | 388.1 | 354 | 405.5 | 228 | 37.5 | 12 |
| VAN 15-A | 3052.0 | 274 | 1773.3 | 182 | 1154.8 | 73 | 1145.0 | 226.6 | 364.8 | 59 |

EXAMPLE 6

Extraction and Fractionation of VAN-10-4 from Calendula Plant Powder

Description (a) Soxhlet 500 g of powder was extracted using either pet ether (60–80) or chloroform. The extraction period was usually around 5 days regardless of solvent used. The volume of solvent was around 3 liters and the crude yield was~60 g (pet ether) or~80 g (chloroform). The crude was combined with an equal amount of silica and left to dry to a powder form over another 5 day period. The total powder obtained for each batch was therefore~120 g (pet ether) or 160 g (chloroform).

(b) VLC 30 g of the crude/silica powder was layered on top of a silica (60 Hgel) VLC column appropriately 5 cm deep×10 cm wide. This was covered with a layer of fine sand and fractionated using the following solvent system.

5×200 ml 50% chloroform: pet ether (60–80)
5×200 ml 70% chloroform: pet ether
5×200 ml 100% chloroform
5×200 ml 10% methanol: chloroform This last step yields the fractions containing VAN-10-4. TLC has confirmed that all of the VAN-10-4 has been removed from the VLC column at this stage. The relevant fractions were rotary evaporated to dryness. Weight of sample obtained is about 2–3 gms.

(c) Sephadex

The inclusion of the Sephadex column at this stage has allowed a much more rapid method of purifying the VLC sample. The sample was redissolved in chloroform and loaded onto the column. The column used was 20 cms high×2 cms wide and contained 13 gm Sephadex (lipophilic LH-20-100). The sample was eluted using 10% pet ether: chloroform using a flow rate of 2–3 ml/min and samples were collected at 1 minute intervals. The presence of VAN-10-4 was confirmed by TLC and the relevant fractions bulked and rotary evaporated. Weight of sample obtained is around 500 mgs.

(d) Silica

A small silica column was used. A 50 ml burette was filled with 20 g silica prepared as a slurry in pet ether (60–80). The sample was redissolved in chloroform and loaded onto the column. The column was 40 cm high×10 cm wide. The sample was eluted using the following solvent system:

10 ml volumes used: flow rate 1 ml/min: fractions collected at 1 minute intervals.

Pet ether (60–80)
10% chloroform: ether
20% chloroform: ether
40% chloroform: ether
50% chloroform: ether (sample starts separating)
60% chloroform: ether
70% chloroform: ether
80% chloroform: ether
90% chloroform: ether
100% chloroform
10% ethyl acetate: chloroform
20% ethyl acetate: chloroform
30% ethyl acetate: chloroform
40% ethyl acetate: chloroform (sample eluting)
50% ethyl acetate: chloroform
50% ethyl acetate: chloroform contained until all VAN-10-4 eluted from the column. This was confirmed by TLC.

This method yields samples containing VAN-10-4+ various impurities (semi-purified samples).

EXAMPLE 7

Treatment of Psoriasis with Extract of Calendula Officinalis

Materials

1. Extraction of plant material. The preparation consisted of a chloroform spirit (5% v/v chloroform in absolute ethanol) extract of the plant material in the ratio 20 g dried plant material extracted with 100 ml of solvent.

2. Preparation of cream. The extract prepared as above was evaporated to dryness and weighed. The weight of "dry" extract was mixed with sufficient aqueous cream B.P. to make 100 g of cream which has a yellow/orange colour.

3. Preparation of the placebo cream. The placebo cream was prepared by adding sufficient quantity of betacarotene to aqueous cream B.P. to yield a product of approximately the same colour as that containing the natural drug.

An extract of plant material obtained from Calendula Officinalis (SSSB) has been found to be clinically useful in treating cases of psoriasis.

Following an extended period of empirical observations on patients a double blind clinical trial was performed on a group of seven patients with psoriasis. The patients (4 male, 3 female) were aged from 53 to 63, except one who was 26. They had the disease from 8.5 to 25 years. Treatment was monitored by a series of pre- and post-trial photographs and by using a "psoriasis symptom score" before and after treatment. The treatment was applied twice daily as a cream for four weeks, and there were three treatments: SSSB, Betnovate, and placebo.

The results of the trial are shown in FIG. 2. The average pretreatment score was 11.1, and this was reduced to 3.5 after SSSB treatment, while it was 5.5 and 7.4 after Betnovate and placebo, respectively.

EXAMPLE 8

Isolation and Purification of VAN-10-4

15 to 30 g of soxhlet extracted crude as performed in example 6 was redissolved in 15 mls of 50% ethyl acetate: 50% hexane. This material was loaded onto a flash 74 column (Biotage Limited) and eluted at a flow rate of 150–200 ml/min using 50% ethyl acetate: 50% hexane as the mobile phase. Time to elution of the VAN compounds from the flash column was estimated by TLC. A diluted solution of the crude mixture (re-dissolved in ethyl acetate) was spotted onto a TLC plate (silica gel 60). The VAN compound mixture was visualised using a standard vannilin: conc. sulphuric acid developer (1 gram vannilin: 100 mls conc. sulphuric acid) and the Rf value calculated. The TLC mobile phase was adjusted by manipulating the ratio of polar: non-polar solvent until the Rf value was around 3.0. The equivalent column volume is worked out from the Rf value according to manufacturers instructions (Biotage Limited). The column volume for the flash 75 system is around 1 liter and the mobile phase giving suitable Rf values was 50% ethyl acetate: 50% hexane.

When this method was tested using the flash 75 column, VAN compounds eluted in fractions 15–19 (equivalent to 4–5 column volumes) Each fraction collected was 250 mls. In a repeat run, under similar conditions, VAN compounds eluted in fractions 14–18. These fractions were combined and evaporated to dryness giving an approximate yield of 200–400 mgs of semi-crude material. This semi-crude material was purified by HPLC using a reverse-phase spherisorb column. A stock solution of the semi-crude material was prepared as 25 mg/ml in acetonitrile and 200 μl aliquots were processed isocratically. The mobile phase used was 75% acetonitrile: 25% water and the flow rate was 5 ml/min. Each sample run was 17 minutes and VAN-10-4 eluted at approximately 14 minutes. NMR spectroscopy confirmed that the eluate was VAN-10-4.

EXAMPLE 9

Extraction of Calendula Officinalis—1 kg Scale

Dried petals of Calendula Officianalis (1 kg) were milled to a coarse powder and extracted continuously with heptane (1–4 liters) i.e. the heptane was continuously distilled from the extract and percolated through the petal mass. The extract was concentrated under vacuum to a volume 500 ml. The resulting concentrate was extracted three times with 500 ml acetonitrile/water solution, 9:1 (v/v). The VAN containing acetonitrile fractions were combined and the acetonitrile removed by vacuum distillation. The resulting orange gum was redissolved. in 500 ml ethyl acetate and washed successively with 500 ml (0.1 M) saturated sodium bicarbonate, 500 ml water, 500 ml (0.1 M) hydrochloric acid and finally 500 ml water. The ethyl acetate solution was then distilled under vacuum to give 10 g of an orange oil.

What is claimed is:

1. A method of treating a skin disease involving hyperproliferation of dermis cells in a mammal which comprises administering to the said mammal an effective, non-toxic amount of a compound of general Formula (I):

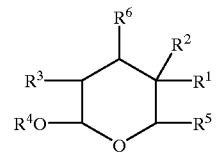

(I)

wherein $R^1$ and $R^2$ are independently selected from H, —OH

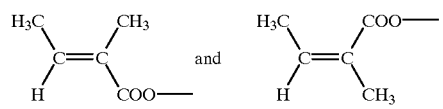

and related esters and ethers thereto;

$R^3$ is selected from —OH,

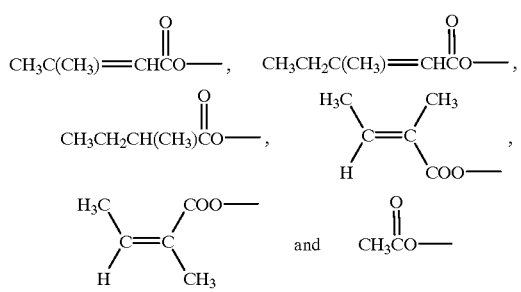

and related esters and ethers thereto;

$R^4$ is

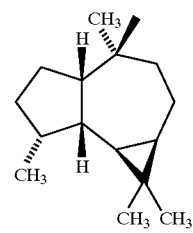

$R^5$ is selected from the group —$CH_3$, —CHO, —COOH, —$CH_2OH$ and related esters and ethers thereto; and $R^6$ is selected from —OH,

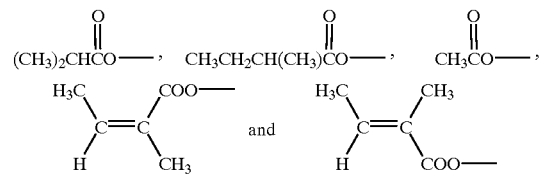

2. A method according to claim 1, wherein in said compound of Formula (I)

$R^1$ and $R^2$ are independently selected from H, —OH

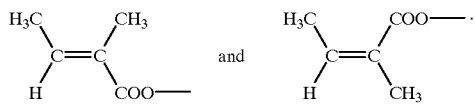 and

3. A method according to claim 2, wherein in said compound of Formula (I)
$R^3$ is selected from —OH,

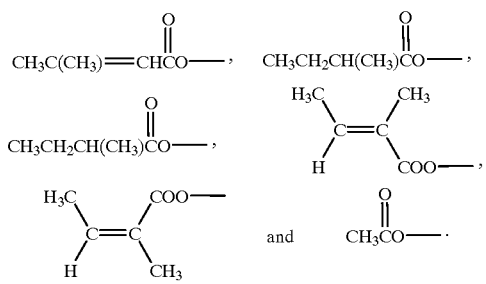

and

4. A method according to claim 1, wherein in said compound of Formula (I) $R^5$ is selected from the group —CH$_3$, —CHO, —COOH, and —CH$_2$OH.

5. A method according to claim 1, wherein in said compound of Formula (I) $R^6$ is selected from

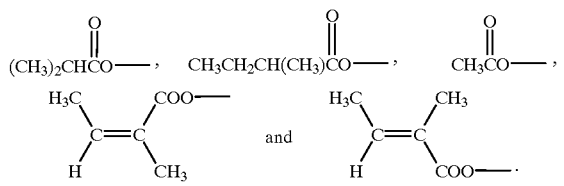

6. A method according to claim 1, wherein in said compound of Formula (I)
$R^1$ and $R^2$ are independently selected from H, —OH (βOH or αOH);
$R^3$ is selected from —OH,

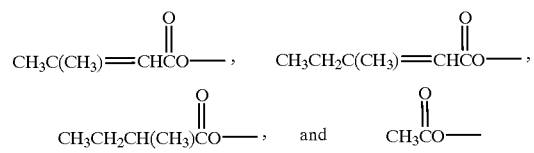

and
$R^4$ is

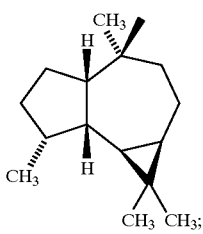

$R^5$ is —CH$_3$; and $R^6$ is selected from —OH,

7. A method according to claim 6, wherein in said compound of Formula (I)
$R^1$ and $R^2$ are independently selected from H and OH (βOH or αOH);
$R^3$ is selected from —OH and (E)-3-methylpent-2-enoate i.e.

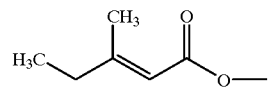

$R^1$ is

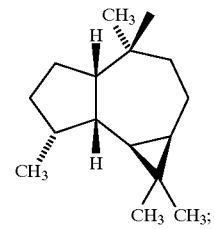

$R^5$ is —CH$_3$; and
$R^6$ is —OH.

8. A method according to claim 1, for the treatment of psoriasis.

9. A method according to claim 1, wherein said compound of Formula (I) is:

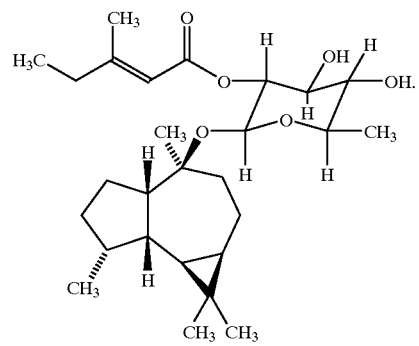

10. A method according to claim 1, wherein said compound of Formula (I) is:

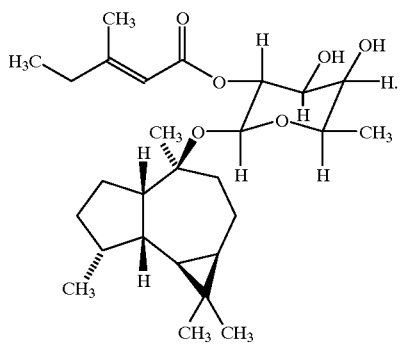

11. A method according to claim 1, wherein said compound of Formula (I) is:

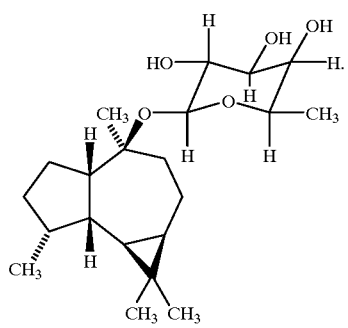

12. A method of manufacturing a medicament for use in treating psoriasis in a mammal comprising the steps of isolating a compound of Formula (I) according to claim 1, and bringing said compound into intimate admixture with a pharmaceutically acceptable carrier therefor.

13. A method according to claim 12 wherein the compound is isolated from *Calendula officinalis* and/or *Calendula persica*.

14. A method according to claim 13 wherein the compound is isolated from *Calendula officinalis*.

15. A pharmaceutical formulation suitable for use in the treatment of psoriasis comprising at least one compound isolated from at least one Calendula species according to Formula (I) as defined in claim 1, wherein $R^4$ of Formula (I) is

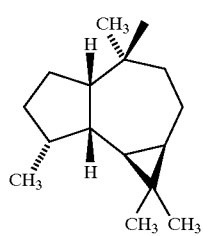

in admixture with a pharmaceutically acceptable carrier.

16. A formulation according to claim 15, wherein the at least one compound according to Formula (I) is isolated and/or purified from an extract derived from at least one Calendula species.

17. A formulation according to claim 16 wherein the at least one compound is isolated and/or purified from an extract derived from at least one of *Calendula persica* and *Calendula officinalis*.

18. A formulation according to claim 17 wherein the at least one compound is isolated and/or purified from an extract of *Calendula officinalis*.

19. A formulation according to claim 15, wherein the at least one compound according to Formula (I) is:

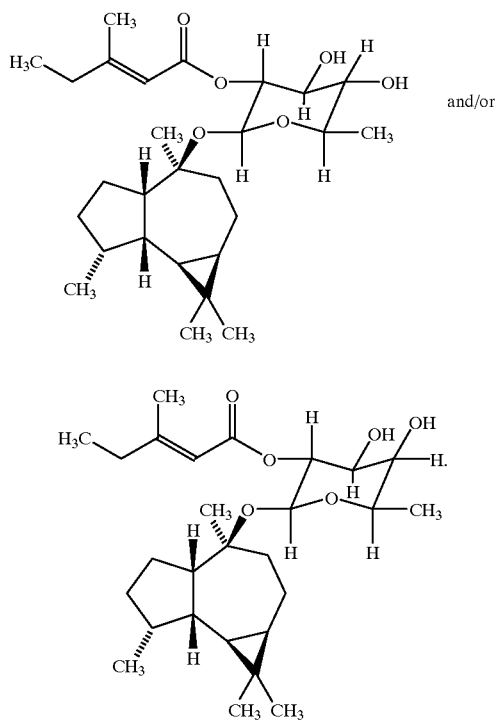

and/or

20. A formulation according to claim 19, wherein the at least one compound is:

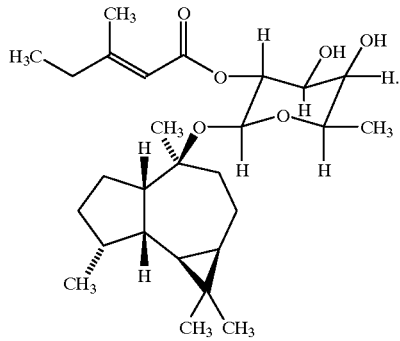

21. A compound of Formula (I):
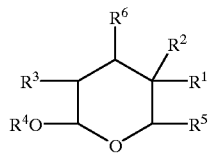
(I)
wherein
$R^1$ and $R^2$ are independently selected from H and —OH;
$R^3$ is (E)-3-methylpent-2-enoate
$R^4$ is
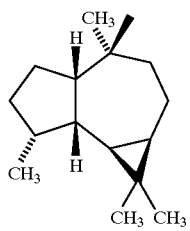
$R^5$ is —CH$_3$; and
$R^6$ is —OH.
22. A compound according to claim 21 which is
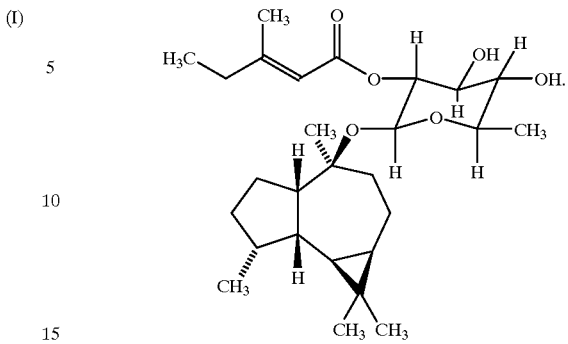
23. A compound according to claim 21 which is
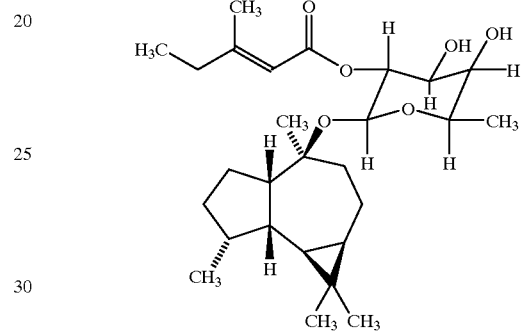
* * * * *

UNITED STATES PATENT AND TRADEMARK OFFICE
CERTIFICATE OF CORRECTION

PATENT NO.   : 6,313,099 B1
DATED        : November 6, 2001
INVENTOR(S)  : Solomon Habtemariam et al.

It is certified that error appears in the above-identified patent and that said Letters Patent is hereby corrected as shown below:

Title page,
The title page showing the illustrative figure should be deleted to be replaced with the attached title page.
Item [56], References Cited, OTHER PUBLICATIONS,
"ble" should read -- blue --; and "Sequiterpene" should read -- Sesquiterpene --.
Item [57] ABSTRACT, line 6, "-H" should read -- –OH --.

Drawings,
Drawing sheets, consisting of Figs. 1 and 2 should be deleted to be replaced with the drawing sheets, consisting of Figs. 1-2, as shown on the attached page.

Column 16,
In the table, second column,
Line 1, cancel "0.65 m";
Line 2, insert -- 0.65 m --.

Columns 19-20, Table 2,
Fourth column, line 3, "3759.8" should read -- 2759.8 --;
Tenth column, line 5, "24.8" should read -- 21.8 --.

Column 23,
Line 54, cancel -- and --.

Column 24,
Line 27, "$R^1$" should read -- $R^4$ --.

Signed and Sealed this

Twenty-eighth Day of May, 2002

*Attest:*

JAMES E. ROGAN
*Director of the United States Patent and Trademark Office*

*Attesting Officer*

United States Patent
Habtemariam et al.

(10) Patent No.: US 6,313,099 B1
(45) Date of Patent: *Nov. 6, 2001

(54) USE OF STEREOISOMERS OF CALENDULA GYLCOSIDES FOR THE TREATMENT OF PSORIASIS

(75) Inventors: Solomon Habtemariam, London; William Howard Stimson, Glasgow; Alexander Irvine Gray, Glasgow; Chaman Lal Anand, Glasgow; Peter George Waterman, Johnstone, all of (GB)

(73) Assignee: University of Strathclyde, Glasglow (GB)

(*) Notice: Subject to any disclaimer, the term of this patent is extended or adjusted under 35 U.S.C. 154(b) by 0 days.

This patent is subject to a terminal disclaimer.

(21) Appl. No.: 09/355,056
(22) PCT Filed: Jan. 23, 1998
(86) PCT No.: PCT/GB98/00183
§ 371 Date: Jan. 24, 2000
§ 102(e) Date: Jan. 24, 2000
(87) PCT Pub. No.: WO98/32761
PCT Pub. Date: Jul. 30, 1998

(30) Foreign Application Priority Data

Jan. 24, 1997 (GB) .................................. 9701415

(51) Int. Cl.[7] ................................. A61K 31/70
(52) U.S. Cl. .................... 514/25; 514/27; 514/860; 514/861; 514/863; 514/864; 536/4.1; 536/18.1
(58) Field of Search .................... 514/25, 27, 860, 514/861, 863, 864; 536/4.1, 18.1

(56) References Cited

FOREIGN PATENT DOCUMENTS

| 38 36 519A1 | 5/1990 | (DE) . |
|---|---|---|
| 63041495 | * 2/1988 | (JP) . |
| WO89/05651A1 | 6/1989 | (WO) . |
| WO91/15218A1 | 10/1991 | (WO) . |
| WO97/04788A2 | 2/1997 | (WO) . |

OTHER PUBLICATIONS

Takaoka et al. "The Structures of Sesquiterpene Glycosides from *Pittosporum tobira* Ait", Chemistry Letters, vol. 7: 1121–1124, 1986.*

Takaoka et al., The structures of sesquiterpene glycosides from *Pittosporum tobira* Ait, Tennen Yuki Kagobutsu Toronkai Koen Yoshishu, vol. 28: 240–247, 1986.*

Etoh et al. "Stilbene glucoside esters and their related compounds as repellants against the ble mussel, *Mytilus edulis*", Nippon Kagaku Kaishi, vol. 5: 542–547, 1991.*

"Sequiterpene Glycosides Based On The Alloaromaden-Drane Skeleton From *CalendulaArvensis*"; Phytochemistry; vol. 27, No. 7; 1988; pp. 2205–2208.

"Sesquiterpene Glycosides From *CalendulaPersica*"; Planta Medica; vol. 54, No. 3, Jun. 1988; pp. 254–256.

"Structure And In Vitro Antiviral Activity Of Sesquiterpene Glycosides From *CalendulaArvensis*"; Journal Of Natural Products; vol. 53, No. 4, Jul. 1990; pp. 830–835.

* cited by examiner

Primary Examiner—Ralph Gitomer
Assistant Examiner—D. Khare
(74) Attorney, Agent, or Firm—Alston & Bird LLP

(57) ABSTRACT

Use of stereoisomeric glycosidic compounds of formula (I) as pharmaceutical agents against psoriasis, compounds therefor and pharmaceutical formulations thereof wherein $R^1$ and $R^2$ are independently selected from —H, —OH, (1) and (2) and related esters and ethers thereto; $R^3$ is selected from —H, (3), (4), (5), (6), (7) and (8) and related esters and ethers thereto; $R^4$ is (9); $R^5$ is selected from the group

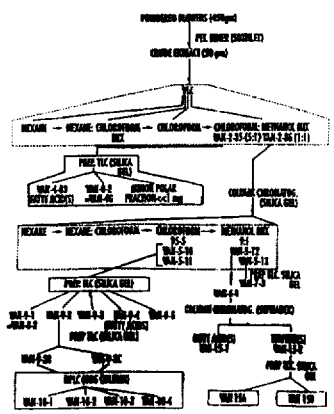

COMPARISON OF THE EFFECT OF SSSB CREAM, BETNOVATE AND PLACEBO IN A GROUP OF 7 PATIENTS WITH PSORIASIS. THE SYMPTOM SCORE IS DERIVED FROM GRADING 10 SYMPTOMS ON A SCALE OF 0 TO 3: ITCH, IRRITATION, RAWNESS OF SKIN, FEELING OF HEAT, BLEEDING, SCALING, DISTURBED SLEEP, SCRATCHY FEELING, COSMETIC ANXIETY, AND PAIN IN SKIN LESIONS.

UNITED STATES PATENT AND TRADEMARK OFFICE
CERTIFICATE OF CORRECTION

PATENT NO.    : 6,313,099 B1
DATED         : November 6, 2001
INVENTOR(S)   : Habtemariam et al.

It is certified that error appears in the above-identified patent and that said Letters Patent is hereby corrected as shown below:

Column 7,
Lines 5-16, the chemical structure should appear as follows:

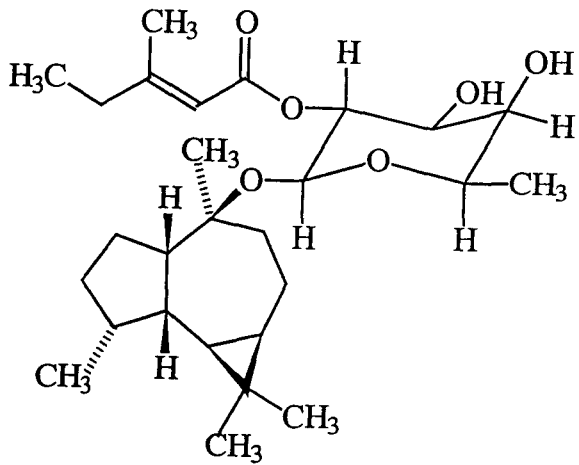

Signed and Sealed this

Fourth Day of February, 2003

JAMES E. ROGAN
*Director of the United States Patent and Trademark Office*